(12) United States Patent
Sanchez et al.

(10) Patent No.: US 10,463,330 B2
(45) Date of Patent: Nov. 5, 2019

(54) POSITIONING AND EVALUATION FOR MANDIBLE OF PATIENT

(71) Applicant: Swissray International, Inc., Piscataway, NJ (US)

(72) Inventors: Thomas Victor Sanchez, Piscataway, NJ (US); Chad Allen Dudzek, Piscataway, NJ (US)

(*) Notice: Subject to any disclaimer, the term of this patent is extended or adjusted under 35 U.S.C. 154(b) by 325 days.

(21) Appl. No.: 15/491,008

(22) Filed: Apr. 19, 2017

(65) Prior Publication Data

US 2017/0303875 A1    Oct. 26, 2017

Related U.S. Application Data

(60) Provisional application No. 62/324,895, filed on Apr. 20, 2016.

(51) Int. Cl.
*A61B 6/04* (2006.01)
*A61B 6/00* (2006.01)

(52) U.S. Cl.
CPC ............ *A61B 6/482* (2013.01); *A61B 6/0407* (2013.01); *A61B 6/501* (2013.01); *A61B 6/505* (2013.01); *A61B 6/58* (2013.01)

(58) Field of Classification Search
CPC ....... A61B 6/0407; A61B 6/482; A61B 6/501; A61B 6/505; A61B 6/58
See application file for complete search history.

(56) References Cited

U.S. PATENT DOCUMENTS

| | | | |
|---|---|---|---|
| 2012/0043475 A1* | 2/2012 | Ahn | A61B 6/04 250/453.11 |
| 2014/0128717 A1* | 5/2014 | Lytle | A61B 6/04 600/407 |
| 2015/0297158 A1* | 10/2015 | Bothorel | A61B 6/06 378/20 |

* cited by examiner

*Primary Examiner* — Mark R Gaworecki (57) ABSTRACT

A system includes a head supporting device, an alignment checker and a scanning device. The head supporting device is disposed on a first surface of an examination table for supporting a patient. The head supporting device includes an adjustable headrest platform for supporting a head of the patient. The adjustable headrest platform is configured to be movable along a direction perpendicular to the first surface of the examination table. The alignment checker is disposed on the examination table. The alignment checker is located corresponding to the head of the patient. The alignment checker is configured to verify a location or an orientation of the head of the patient. The scanning device is configured for capturing a scan image corresponding to a mandible of the patient.

17 Claims, 10 Drawing Sheets

POSITIONING AND EVALUATION FOR MANDIBLE OF PATIENT

RELATED APPLICATIONS

This application claims priority to U.S. Provisional Application Ser. No. 62/324,895, filed Apr. 20, 2016, which is herein incorporated by reference.

BACKGROUND

Field of Invention

The present application relates to a system and a method for health care. More particularly, the present application relates to a system and a method for evaluating regions of interest on a patient.

Description of Related Art

In order to diagnosis or monitor an internal condition of the patient, a radiation scanner is usually utilized to scan particular regions of interest on a patient. The radiation scanner can be utilized on the mandible of the patient to evaluate the bone mineral content.

Typically, the clinicians are required to diagnosis according to current scan results and previous medical records of the patients. However, it is hard for clinicians to notice a minor variation of the bone mineral content at the very beginning of a disease.

In addition, two scanning examinations to the same patient may be performed at different time spots with different operators, and the patient may be examined with different gestures or positions between these two scanning examinations. All these factors will affect the scanning results, such that it is even harder to distinguish that a variation between two scanning results is caused by a potential disease or simply a measurement error.

SUMMARY

An embodiment of the disclosure provides a system for evaluating a patient. The system includes a head supporting device, an alignment checker and a scanning device. The head supporting device is disposed on a first surface of an examination table for supporting the patient. The head supporting device includes an adjustable headrest platform for supporting a head of the patient. The adjustable headrest platform is configured to be movable along a direction perpendicular to the first surface of the examination table. The alignment checker is disposed on the examination table. The alignment checker is located corresponding to the head of the patient. The alignment checker is configured to verify a location or an orientation of the head of the patient. The scanning device is configured for capturing a scan image corresponding to a mandible of the patient.

In an embodiment of the disclosure, the scanning device includes a radiation emitting member and a radiation detecting member. The radiation emitting member is configured for generating a scanning radiation in a route perpendicular to the first surface of the examination table. The route penetrates the mandible. The radiation detecting member is configured for sensing the scanning radiation to generate the scan image. The radiation emitting member and the radiation detecting member are disposed on opposite sides relative to the examination table.

In an embodiment of the disclosure, when the patient is laid in a lateral recumbent position on the first surface, the adjustable headrest platform is configured to support at least a part of a temporal region or a parietal region of the head.

In an embodiment of the disclosure, when the adjustable headrest platform is moved along the direction perpendicular to the first surface, a height level of the adjustable headrest platform is adjusted, and the neck of the patient is flexible to rotate rightward or leftward according to the height level of the adjustable headrest platform.

In an embodiment of the disclosure, the alignment checker includes a positioning grid. The positioning grid includes a standing base and a transparent plate connected on the standing base. The transparent plate is located corresponding to a facial region of the patient. Marking grid lines are labeled on the transparent plate. The location or the orientation of the head of the patient is verified by comparing facial features or facial contours to the marking grid lines.

In an embodiment of the disclosure, when the facial features or the facial contours are tilted by a tilt angle in reference to the marking grid lines, the adjustable headrest platform is moved from a first height level to a second height level according to the tilt angle. A difference between the first height level and the second height level is positively correlated to the tilt angle.

In an embodiment of the disclosure, the scanning device further includes a processing unit. When a first scan is performed on the patient, the processing unit is configured to evaluate the scan image to locate a chin point of the mandible, detect a body area and a ramus area of the mandible in the scan image, search for a first region of interest in the body area and a second region of interest in the ramus area, calculate first coordinates of the first region of interest relative to the chin point and second coordinates of the second region of interest relative to the chin point, and store the first coordinates and the second coordinates in a scan record corresponding to the patient.

In an embodiment of the disclosure, when a second scan is performed on the patient after the first scan, the processing unit is adapted to locate the chin point of the mandible in the scan image, read the scan record corresponding to the patient, search for the first region of interest in the body area and the second region of interest in the ramus area, calculate third coordinates of the first region of interest relative to the chin point and fourth coordinates of the second region of interest relative to the chin point, and store the third coordinates into the scan record corresponding to the first region of interest and the fourth coordinates into the scan record corresponding to the second region of interest.

In an embodiment of the disclosure, the processing unit is configured to compare first bone mineral analyzation data of the first coordinates obtained in the first scan with third bone mineral analyzation data of the third coordinates obtained in the second scan to track a first bone mineral variation of the first region of interest in the body area, and compare second bone mineral analyzation data of the second coordinates obtained in the first scan with fourth bone mineral analyzation data of the fourth coordinates obtained in the second scan to track a second bone mineral variation of the second region of interest in the ramus area.

Another embodiment of the disclosure provides a method for evaluating a patient. The method includes following operations. An adjustable headrest platform is provided to support a head of the patient. A location or an orientation of the head of the patient is verified. A height level of the adjustable headrest platform is adjusted according to a verifying result. A scan image corresponding to a mandible of the patient is captured.

In an embodiment of the disclosure, in operation of verifying the location or the orientation of the head of the patient, the method include: comparing facial features or facial contours to marking grid lines labeled on a positioning grid; and, calculating a tilt angle of the facial features or the facial contours in reference to the marking grid lines.

In an embodiment of the disclosure, in operation of adjusting the height level of the adjustable headrest platform according to the verifying result, the method includes moving the adjustable headrest platform from a first height level to a second height level according to the tilt angle. A difference between the first height level and the second height level is positively correlated to the tilt angle.

In an embodiment of the disclosure, when a first scan is performed on the patient, the method further includes: evaluating the scan image to locate a chin point of the mandible; detecting a body area and a ramus area of the mandible in the scan image; searching for a first region of interest in the body area and a second region of interest in the ramus area; calculating first coordinates of the first region of interest relative to the chin point and second coordinates of the second region of interest relative to the chin point; and, storing the first coordinates and the second coordinates in a scan record corresponding to the patient.

In an embodiment of the disclosure, when a second scan is performed on the patient after the first scan, the method further includes locating the chin point of the mandible in the scan image; reading the scan record corresponding to the patient; searching for the first region of interest in the body area and the second region of interest in the ramus area; calculating third coordinates of the first region of interest relative to the chin point and fourth coordinates of the second region of interest relative to the chin point; and, storing the third coordinates into the scan record corresponding to the first region of interest and the fourth coordinates into the scan record corresponding to the second region of interest.

In an embodiment of the disclosure, the method further includes: comparing first bone mineral analyzation data of the first coordinates obtained in the first scan with third bone mineral analyzation data of the third coordinates obtained in the second scan to track a first bone mineral variation of the first region of interest in the body area; and, comparing second bone mineral analyzation data of the second coordinates obtained in the first scan with fourth bone mineral analyzation data of the fourth coordinates obtained in the second scan to track a second bone mineral variation of the second region of interest in the ramus area.

Another embodiment of the disclosure provides a system for positioning the head of a patient for radiation imaging. The system includes adjustable head supporting means, aligning means and adjusting means. The adjustable head supporting means are utilized for providing an adjustable headrest platform movable along a direction. The aligning means are utilized for verifying a location and an orientation of the head of the patient. The adjusting means are utilized for moving the adjustable headrest platform along the direction according to a result generated by the aligning means.

It is to be understood that both the foregoing general description and the following detailed description are by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Reference will now be made in detail to the present embodiments of the disclosure, examples of which are illustrated in the accompanying drawings. Wherever possible, the same reference numbers are used in the drawings and the description to refer to the same or like parts.

Figure 1:
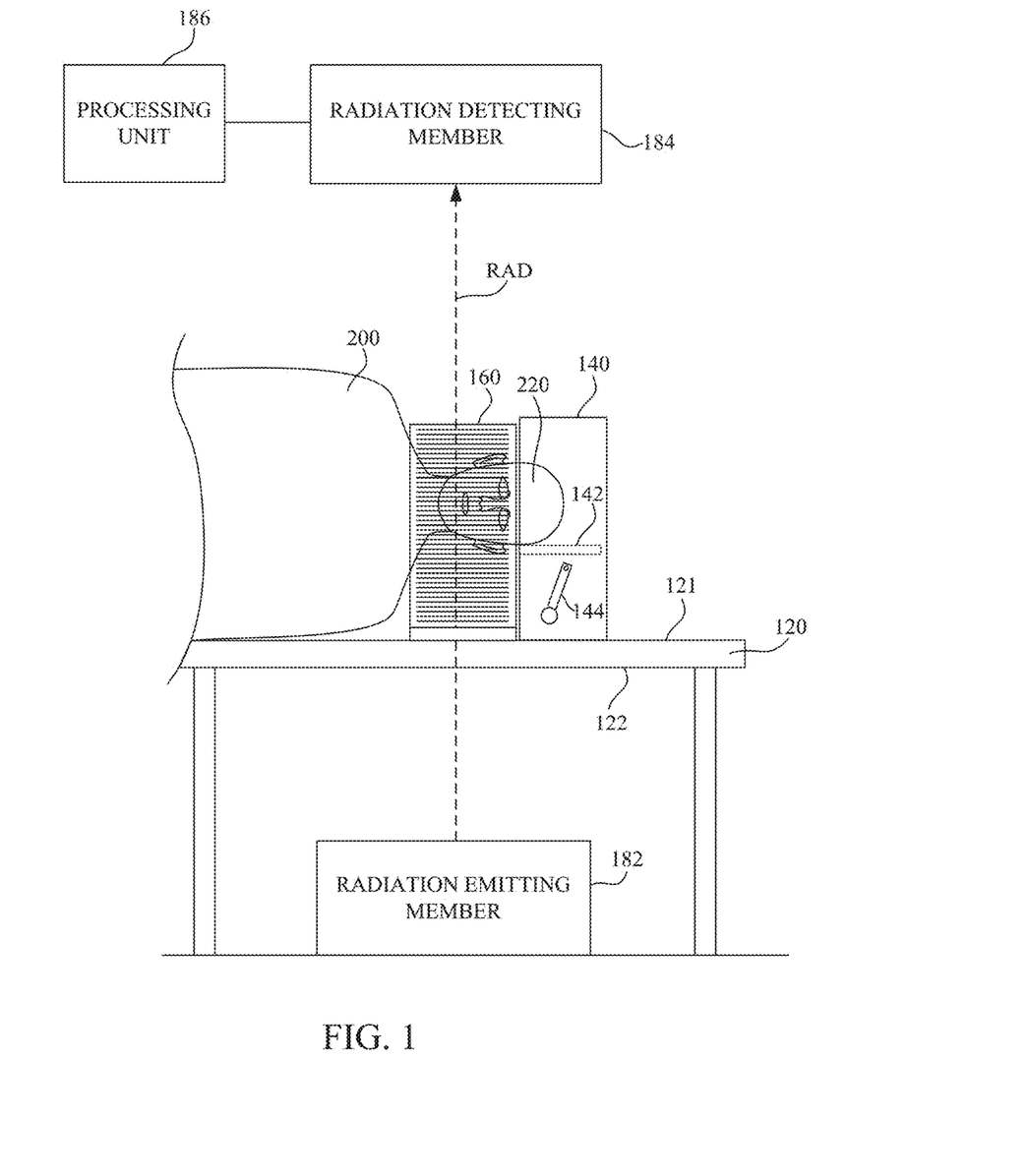
FIG. 1 is a schematic diagram illustrating a system for evaluating a patient according to embodiments of the disclosure.

Reference is made to FIG. 1, which is a schematic diagram illustrating a system 100 for evaluating a patient 200 according to embodiments of the disclosure. In an embodiment, the system 100 is utilized to perform a mandible study related to the patient 200. The mandible study can be performed by an X-ray-based device. In an embodiment, the X-ray-based device can be a Dual-Energy X-ray Absorptiometry (DXA) scanning device capable of quantifying the amount and/or density of bone mineral content existed in regions of a human mandible bone. The system 100 as shown in FIG. 1 includes an examination table 120, a head supporting device 140, an alignment checker 160 and a scanning device. In the embodiment shown in FIG. 1, the scanning device includes a radiation emitting member 182, a radiation detecting member 184 and a processing unit 186. The head supporting device 140 is utilized as a fixture to position the patient's head and mandible bone consistently.

The examination table 120 is utilized to support the patient 200. As shown in FIG. 1, the examination table 120 includes a first surface 121 and a second surface 122. The first surface 121 is the top surface of the examination table 120. In a preparation before the scanning, the patient 200 is guided to lie on the first surface 121 of the examination table 120. The patient 200 is guided to lay on his/her left shoulder and face to the front in the embodiment of FIG. 1, but the disclosure is not limited thereto. The patient 200 can relax and rest his/her head 220 on the adjustable headrest platform 142 of the head supporting device 140. In this embodiment, the patient 200 lays in a lateral recumbent position on the first surface 121, and the adjustable headrest platform 142 is configured to support at least a part of a temporal region or a parietal region of the head 220.

The head supporting device 140 is disposed on the first surface 121 of the examination table 120 for supporting the patient 200. The head supporting device 140 includes the adjustable headrest platform 142 for supporting the head 220 of the patient 200. The adjustable headrest platform 142 is configured to be movable along a direction perpendicular to the first surface 121 of the examination table 120. In other words, the adjustable headrest platform 142 can move upward or downward to different height levels. During aforesaid movement, the adjustable headrest platform 142 may carry the head 220 of the patient 200, such that the neck of the patient 200 is flexible to rotate rightward or leftward according to the height level of the adjustable headrest platform 142.

In the embodiment shown in FIG. 1, the head supporting device 140 is disposed on the right side relative to the patient 200, such that the patient 200 is guided to lay on his/her left shoulder and face to the front, but the disclosure is not limited thereto. In another embodiment, the head supporting device 140 can be disposed on the left side (not shown in figures) relative to the patient 200, such that the patient 200 is guided to lay on his/her right shoulder and face to the front.

The alignment checker 160 is disposed on the first surface 121 of the examination table 120. The alignment checker 160 is located in front of a face region of the head 220 of the patient 200. The alignment checker is configured to verify a location or an orientation of the head 220 of the patient 200.

The scanning device (e.g., the radiation emitting member 182, the radiation detecting member 184 and the processing unit 186) is configured for capturing a scan image corresponding to the mandible of the patient 200. The radiation emitting member 182 is configured for generating a scanning radiation RAD in a route perpendicular to the first surface 121 of the examination table 120. In this embodiment shown in FIG. 1, the route of the scanning radiation RAD penetrates from the left side to the right side of the mandible of the patient 200. The radiation detecting member 184 is configured for sensing the scanning radiation to generate the scan image. The radiation emitting member 182 and the radiation detecting member 184 are disposed on opposite sides relative to the examination table 120. In this embodiment, the radiation emitting member 182 is located under the second surface 122 of the examination table 120, and the radiation detecting member 184 is located above the first surface 121 of the examination table 120, but the disclosure is not limited thereto. The positions of the radiation emitting member 182 and the radiation detecting member 184 can be alternated in another embodiment.

The system 100 may further include a software package executed by the processing unit 186 to perform x-ray acquisition and analysis. A standard location on the mandible bone is defined and measured. Variations of bone mineral content in the mandible bone can be compared over time to monitor rapid changes resulting from disease or treatment.

Figure 2A:
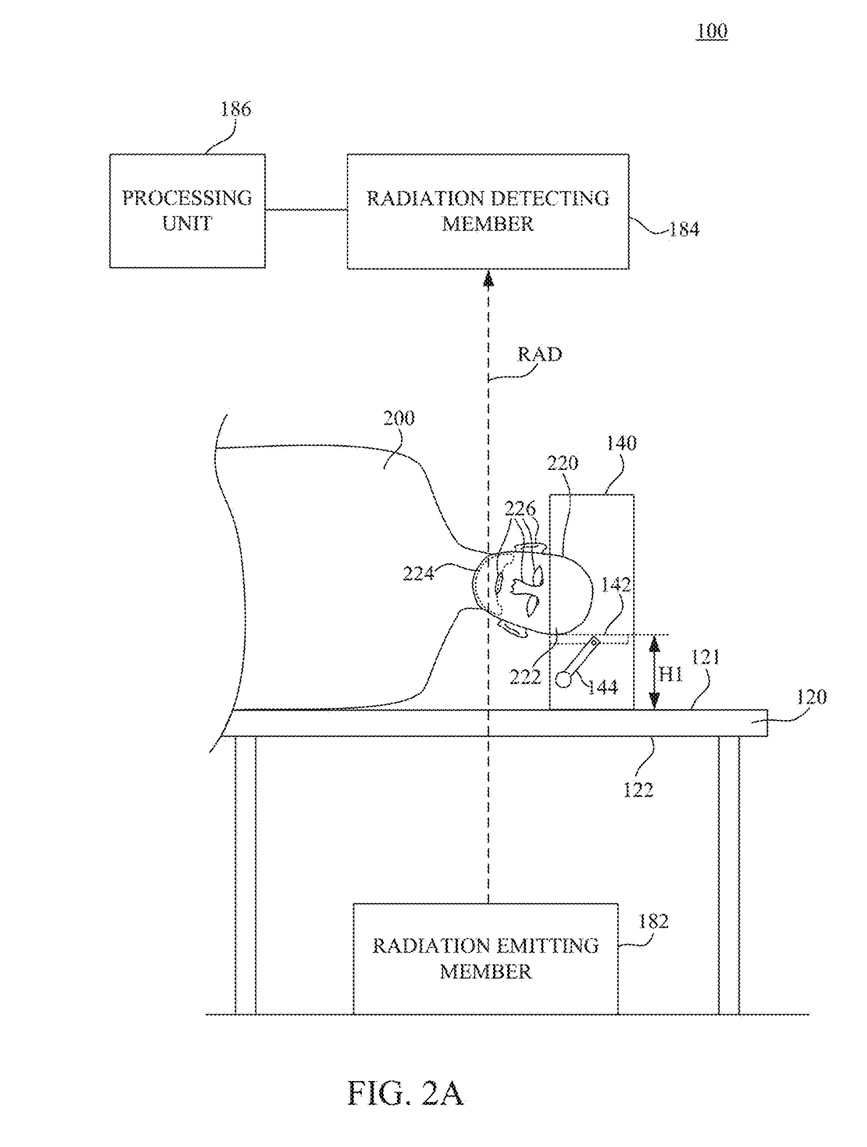
FIG. 2A and FIG. 2B are schematic diagrams illustrating the relationships between the patient and the system when the adjustable headrest platform is adjusted to different height levels.
Figure 2B:
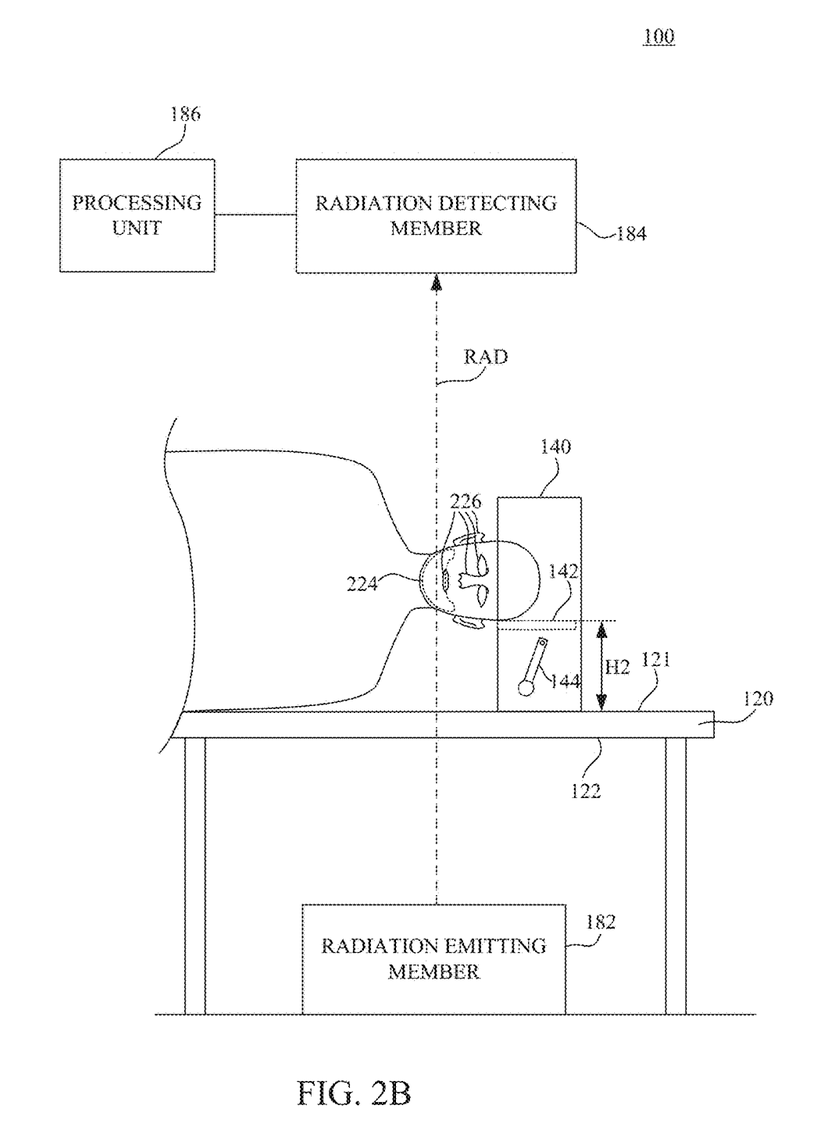
Figure 3:
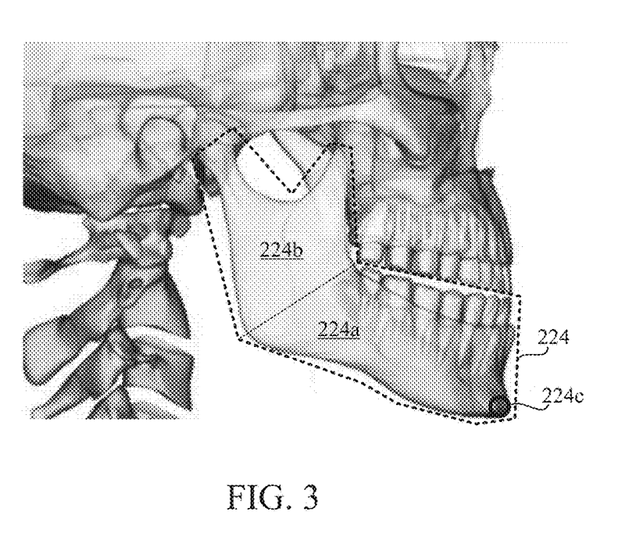
FIG. 3 is a schematic diagram illustrating an example of the scan image of the mandible of the patient captured by the scanning device of the system.

Reference is also made to FIG. 2A, FIG. 2B and FIG. 3. FIG. 2A and FIG. 2B are schematic diagrams illustrating the relationships between the patient 200 and the system 100 when the adjustable headrest platform 142 is adjusted to different height levels. FIG. 3 is a schematic diagram illustrating an example of the scan image of the mandible 224 of the patient 200 captured by the scanning device of the system 100.

In the embodiment shown in FIG. 2A, the adjustable headrest platform 142 is configured at a first height level H1 relative to the first surface 121 of the examination table 120. In the embodiment shown in FIG. 2B, the adjustable headrest platform 142 is configured at a second height level H2 relative to the first surface 121 of the examination table 120.

The mandible 224 of the patient 200 is located inside the jaw of the patient 200. In general, the mandible 224 has a symmetrical structure between the right portion and the left portion of the mandible 224. To capture an effective scan image about the mandible 224, the right portion and the left portion of the mandible 224 shall be superimposed over each other. FIG. 3 illustrates an ideal example of the effective scan image. As shown in FIG. 3, the right portion and the left portion of the mandible 224 are leveled and superimposed over each other, such that the contours of the mandible 224 are clear.

If the right portion and the left portion of the mandible 224 are not leveled, referring to FIG. 2A in which the head 220 of the patient 200 is tilted to the left side and the mandible 224 is rotated correspondingly, the scanning image captured when the right portion and the left portion of the mandible 224 are not leveled with the scanning radiation RAD will have an unclear result, which may include multiple contour borders of the right portion and the left portion of the mandible 224.

If the right portion and the left portion of the mandible 224 are leveled, referring to FIG. 2B in which the head 220 of the patient 200 is not tilted to the left side or to the left side, and the mandible 224 is leveled relative to the scanning radiation RAD. In this case, when the right portion and the left portion of the mandible 224 are leveled and superimposed over each other, the scan image as shown in FIG. 3 can have a clear image about the mandible 224.

Figure 4A:
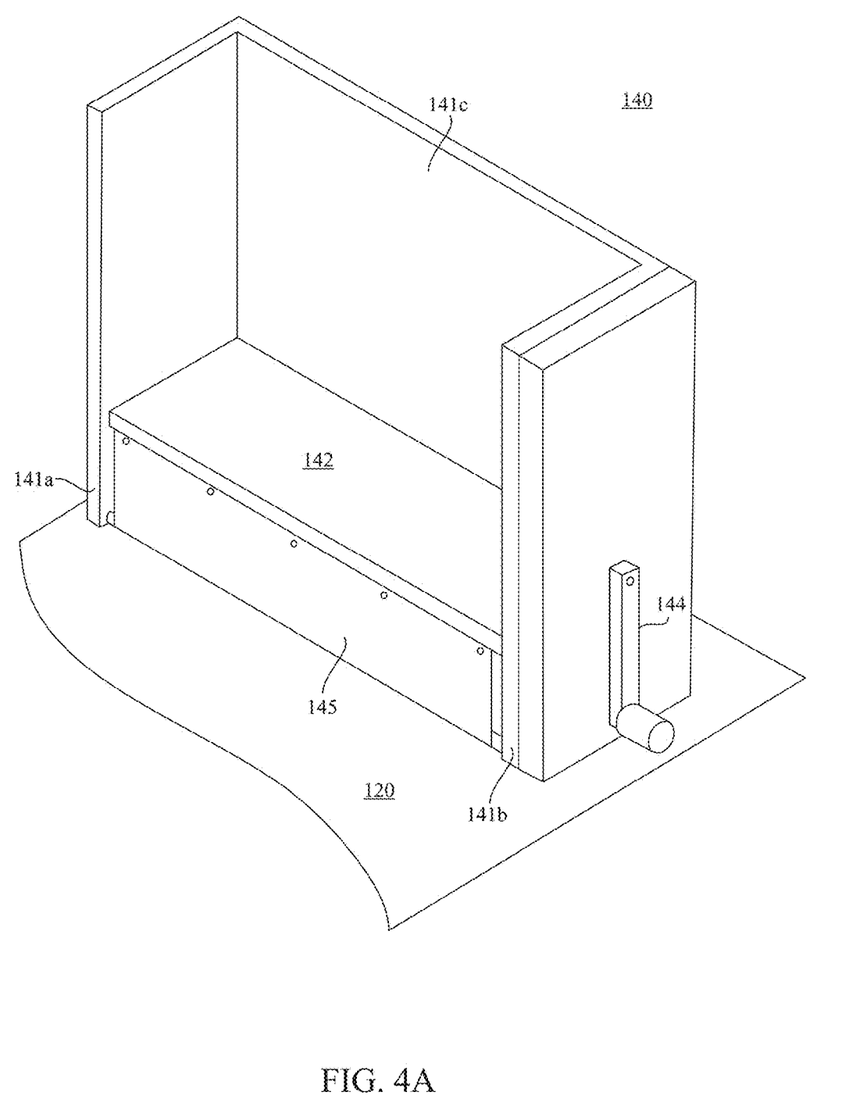
FIG. 4A and FIG. 4B are perspective views illustrating further details of the head supporting device according to an embodiment of the disclosure.
Figure 4B:
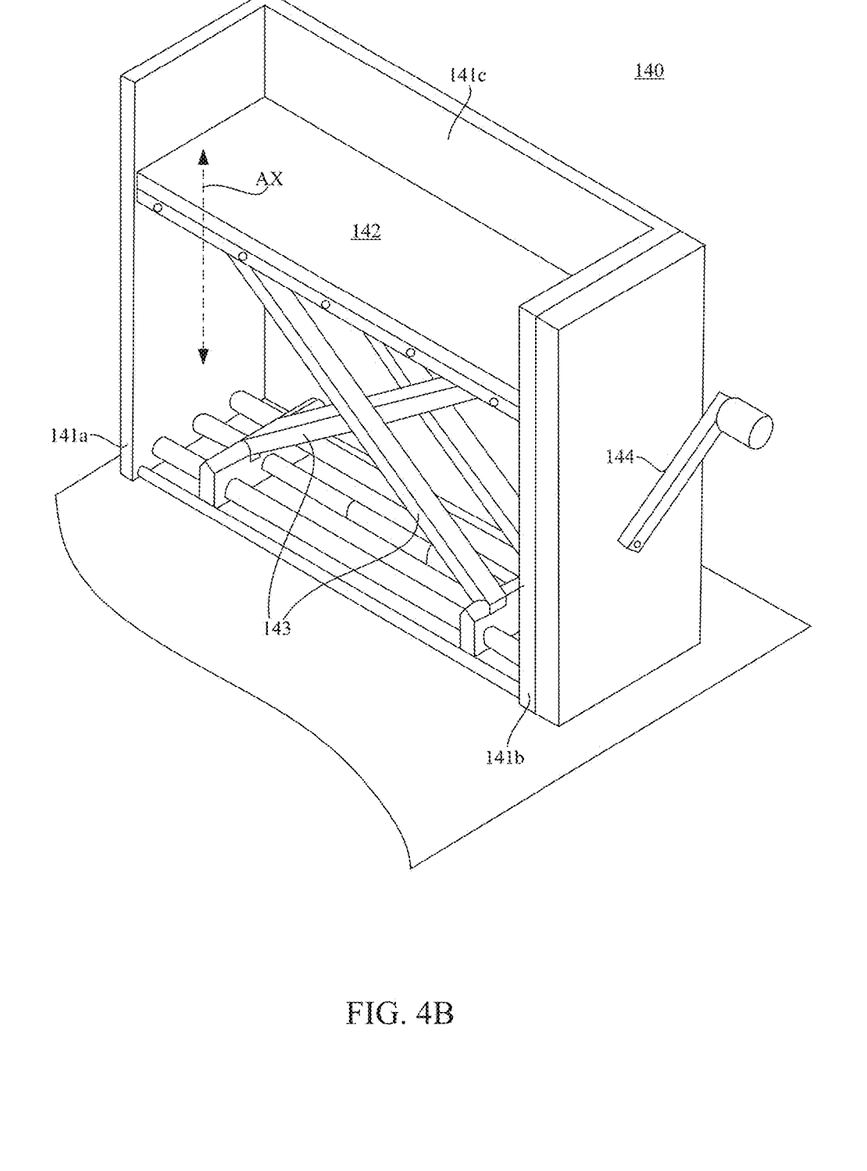
Figure 5:
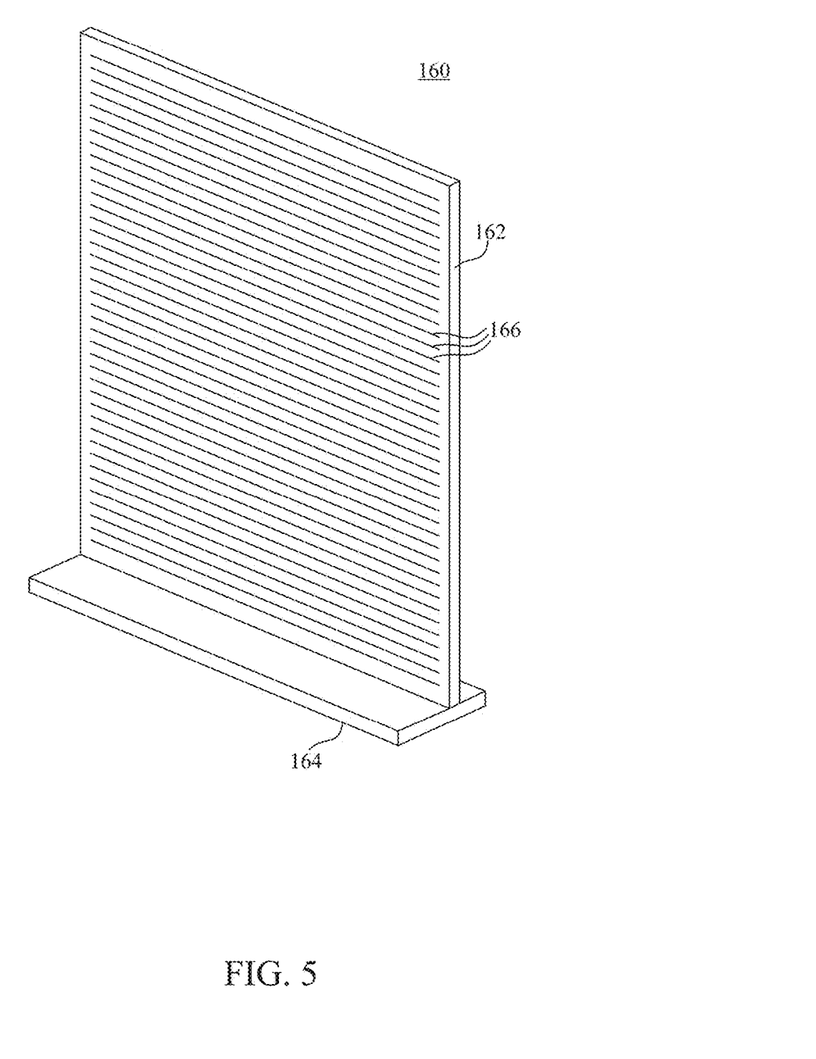
FIG. 5 is a perspective view illustrating further details of the alignment checker according to an embodiment of the disclosure.

As shown in FIG. 1, the head supporting device 140 includes a height level adjuster 144, which is configured to change the height level of the adjustable headrest platform 142. The system 100 includes the alignment checker 160 for verifying the location or the orientation of the head 220 of the patient 200. The head supporting device 140 and the alignment checker 160 cooperates to ensure the right portion and the left portion of the mandible 224 are leveled and superimposed over each other in the scan image. Reference is further made to FIG. 4A, FIG. 4B and FIG. 5. FIG. 4A and FIG. 4B are perspective views illustrating further details of the head supporting device 140 according to an embodiment of the disclosure. FIG. 5 is a perspective view illustrating further details of the alignment checker 160 according to an embodiment of the disclosure.

As shown in FIG. 4A, the head supporting device 140 includes base members (including a right platform support 141a, a left platform support 141b and a back platform support 141c), the adjustable headrest platform 142, the height level adjuster 144 and a protection curtain 145.

The right platform support 141a, the left platform support 141b and the back platform support 141c are fixed on the examination table 120. The height level adjuster 144 can be manipulated to adjust the height level of the adjustable headrest platform 142. The protection curtain 145 is utilized to protect the patient 200 from moving parts inside the head supporting device 140. The protection curtain 145 acts as a screen to keep the patient away from potential injury should they come in contact with the internal components.

As shown in FIG. 4B, the moving parts inside the head supporting device 140 include a lifting member 143. The lifting member 143 is connected between the base member and the adjustable headrest platform 142. In the embodiment shown in FIG. 4B, the lifting member 143 includes a scissor lift structure. The lifting member 143 includes scissor lifting arms, which can be stretched out or contracted to each other. The scissor lift structure provides the mechanics to lift and lower the adjustable headrest platform 142 that is supporting the head 220 in a proper position for following scan and study. The lifting member 143 is configured for carrying the adjustable headrest platform 142 to move to different height levels (e.g., from the first height level H1 in FIG. 2A to the second height level H2 in FIG. 2B) relative to the examination table 120.

In this embodiment, the height level adjuster 144 is pivotally connected on a joint connector located on the left platform support 141b. The height level adjuster 144 can be connected to the lifting member 143 through a dynamic transmission structure (e.g., a chain gear and a gear drive). The gear and gear drive (not shown in figures) provides the mechanics to drive the lifting, lowering and holding in place of the adjustable headrest platform 142. The dynamic transmission structure is not limited thereto. When the height level adjuster 144 is manipulated to rotate clockwise or counter-clockwise, the adjustable headrest platform 142 can be moved upward or downward by the lifting member 143.

As show in FIG. 1 and FIG. 5, the alignment checker 160 may include a positioning grid. The positioning grid includes a standing base 164 and a transparent plate 162 connected on the standing base 164. The transparent plate 162 in FIG. 5 is located corresponding to a facial region of the patient 200 (referring to FIG. 1), and marking grid lines 166 are labeled on the transparent plate 162. The location or the orientation of the head of the patient can verified by comparing facial features or facial contours (referring to the facial features 226 shown in FIG. 2A and FIG. 2B) on the facial region of the patient 200 to the marking grid lines 166.

In an embodiment, the transparent plate 162 can be a clear acrylic plate, and the marking grid lines 166 are positioning aids that allows the operator to confirm when the head is level with the examination table 120 so that the left and right mandibles are properly oriented for following scan and study.

Figure 6A:
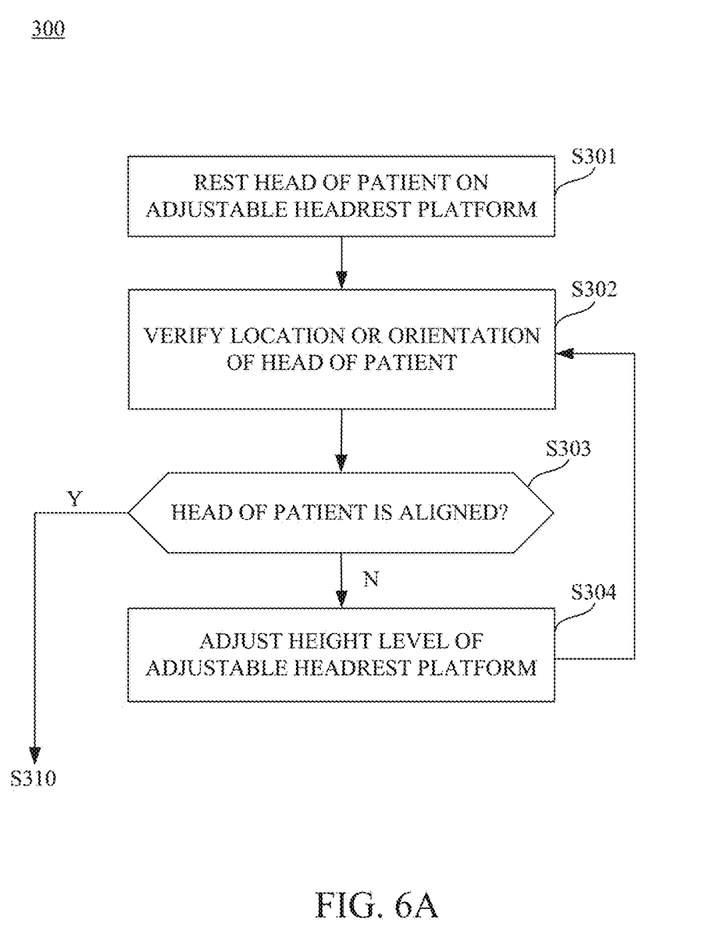
FIG. 6A, FIG. 6B and FIG. 6C are flow chart illustrating a method suitable to be utilized on the system shown in FIG. 1.
Figure 6B:
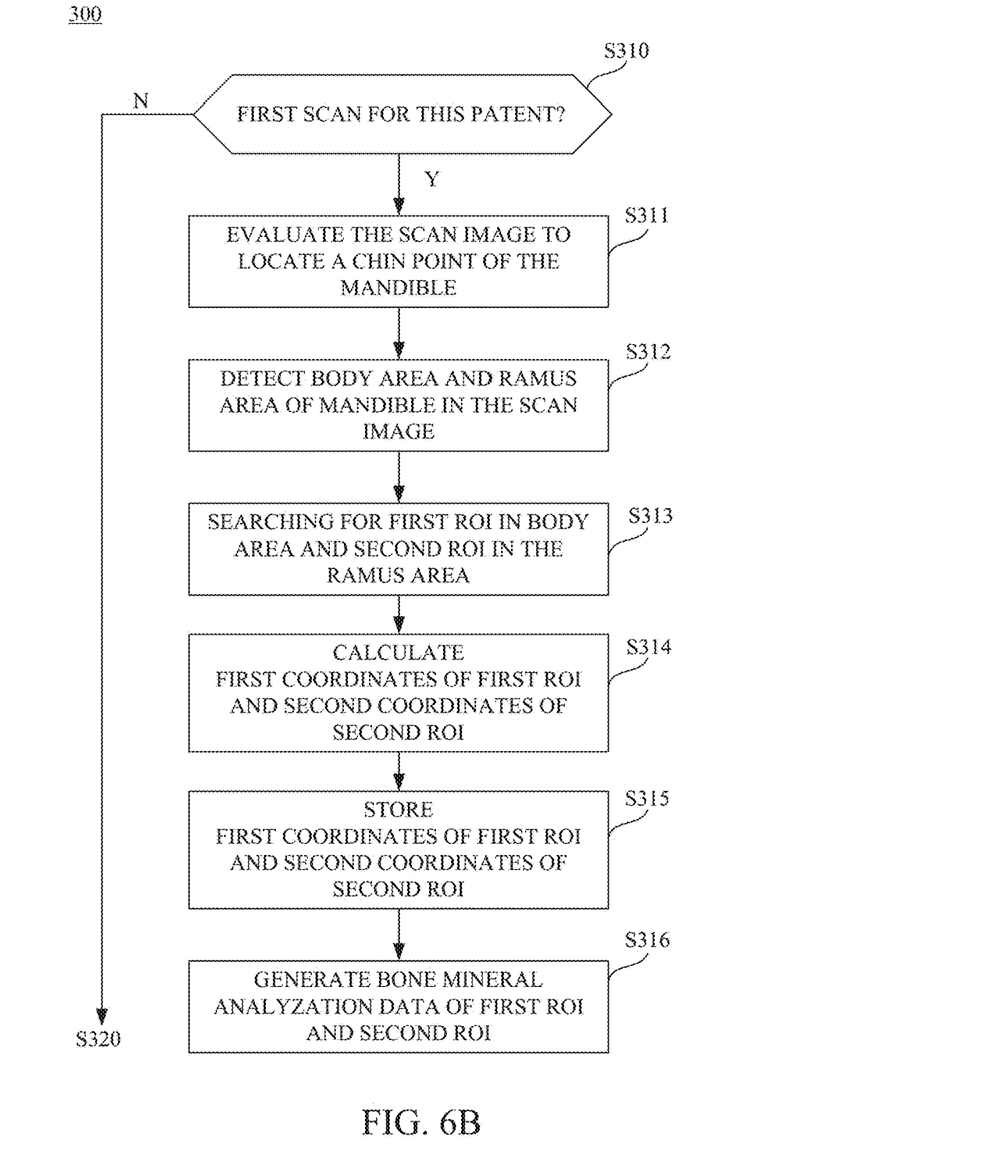
Figure 6C:
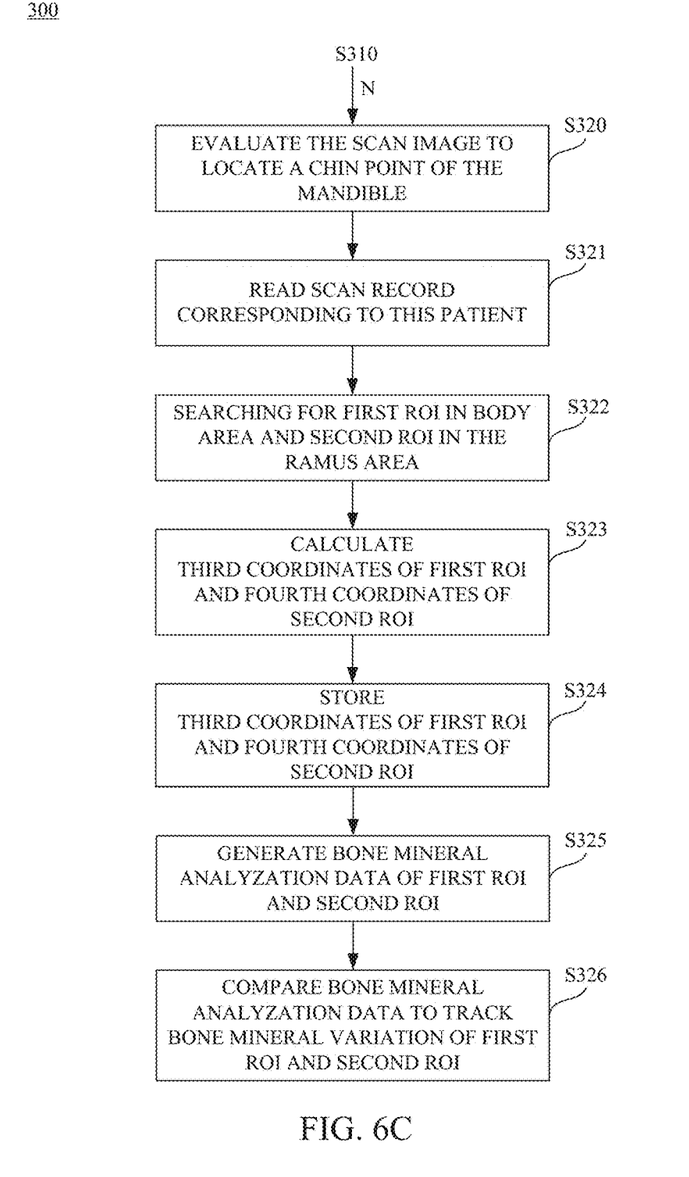

Reference is further made to FIG. 6A, FIG. 6B and FIG. 6C which are flow chart illustrating a method 300 suitable to be utilized on the system 100 shown in FIG. 1 and aforesaid embodiments.

FIG. 6A shows a procedure for preparing the patient. As shown in FIG. 1 and FIG. 6A, the patient 200 is guided to lay in the lateral recumbent position on the examination table 120. Operation S301 is performed to guide the patient to rest his/her head 220 on the adjustable headrest platform 142. Operation S302 is performed to verify the location or the orientation of the head 220 of the patient 200 through the alignment checker 160. The location or the orientation of the head 220 is verified by comparing facial features 226 (referring to the FIG. 2A and FIG. 2B) to the marking grid lines 166 (referring to FIG. 5) labeled on the alignment checker 160. Operation S303 is performed to determine whether the head 220 of the patient is aligned in a proper position or not. The proper position means that the right portion and the left portion of the mandible 224 shall be superimposed over each other related to the scanning radiation RAD as shown in FIG. 2B.

If the user current lay as shown in FIG. 2A, the facial features 226 will not match to the marking grid lines 166, which means that the head 220 of the patient is not aligned in the proper position. In this case, the method 300 can further calculates a tilt angle of the facial features 226 in reference to the marking grid lines 166. When the tilt angle is known, the operation S304 is performed to adjusting a height level of the adjustable headrest platform 142 according to the verifying result. In this embodiment, the adjustable headrest platform 142 is moved according to the tilt angle. For example, the adjustable headrest platform 142 from the first height level H1 shown in FIG. 2A to the second height level H2 in FIG. 2B until the facial features 226 are perfectly matched to the marking grid lines 166. A difference between the first height level H1 in FIG. 2A and the second height level in FIG. 2B is positively correlated to the tilt angle found in the verification in S302. When the facial features 226 is perfectly aligned to the marking grid lines 166 on the alignment checker 160, operation S303 will determine that the head 220 is aligned already, and then the patient 200 is ready for following scan, such that the method 300 proceeds to operations S310.

With most current DXA "table scanners", the x-ray beam on the device travels vertically, typically from the underside of a patient support table where the patient lies down, through the patient, and up to a detector assembly which measures the amount of x-ray passing through the subject. To perform the Mandible study correctly, the mandible bone must be positioned so the left and right halves of the bone are superimposed over each other, relative to the x-ray beam. On a typical DXA table scanner, this would involve the patient being positioned lying on their side. In this position, the patient's head must be elevated and rotated into position, and then prevented from moving for the duration of the x-ray acquisition. Aforesaid embodiment of the disclosure provides for a specific positioning system that supports the patient's head in the proper elevation and rotation.

As developed the device allows for the platform height to be adjusted so as to support the ability to change the angle of the patient's neck. The control of the x-ray acquisition is performed with a software application that controls the location and duration of the x-ray exposure. The software application will also perform the numeric calculations to interpret the amount of x-ray passed through the subject and using DXA methodology will convert those measurements into bone mass. On a pencil-beam DXA scanner, the x-ray beam will scan over the subject area in an S-like pattern, using as many scan lines as necessary to pass over the intended subject area. The resulting scan image should include the entire Mandible bone, parts of the skull and spine adjacent to the mandible, and soft tissue or air in the front and below the chin.

As shown in FIG. 1 and FIG. 6B, operation S310 is executed to determine whether the patient is going through his/her first scan or not. The operation S310 can be determined according to an input from the patient or the clinician or by searching a medical record corresponding to this patient. If the input indicates that it is the first visit of this patent or there is no matched medical record corresponding to this patient, the method 300 proceeds to operations S311 to S316 to perform a first scan on this patient.

As shown in FIG. 1, FIG. 3 and FIG. 6B, operation S311 is performed by the processing unit 186 to evaluate the scan image to locate a chin point 224c of the mandible 224. The chin point 224c can be found by analyzed a border or a boundary of the mandible 224.

As shown in FIG. 1, FIG. 3 and FIG. 6B, operation S312 is performed by the processing unit 186 to evaluate the scan image to detect a body area 224a and a ramus area 224b of the mandible 224 in the scan image. Operation S313 is performed by the processing unit 186 to evaluate the scan image to search for one or more first region of interest (ROI) in the body area 224a and one or more second ROI in the ramus area 224b. Operation S314 is performed by the processing unit 186 to calculate first coordinates of the first ROI(s) relative to the chin point 224c and second coordinates of the second ROI(s) relative to the chin point 224c. Operation S315 is performed by the processing unit 186 to store the first coordinates of the first ROI(s) and the second coordinates of the second ROI(s) in a scan record corresponding to the patient.

Operation S316 is further performed by the processing unit 186 to generate bone mineral analyzation data of first ROI(s) and bone mineral analyzation data of the second ROI(s) corresponding to the patient. The bone mineral analyzation data may include numeric Bone Mass Content (BMC) of all ROIs and/or Bone Mass Density (BMD) of all ROIs. Since this is the first scan to the patient, the analyzation result covers the data about Bone Mass Content and Bone Mass Density of all ROIs found in the body area 224a and the ramus area 224b during this first scan.

At operation S310, if the input indicates that it is a follow-up visit of this patent or a matched medical record is found corresponding to this patient, referring to FIG. 6C the method 300 proceeds to operations S320 to S326 to perform a second scan on this patient. The second scan can be any follow-up scan (the $2^{nd}$ time scan, the $3^{rd}$ time scan or any following scan) after the first scan to the same patient.

As shown in FIG. 1, FIG. 3 and FIG. 6C, operation S320 is performed by the processing unit 186 to evaluate the scan image to locate the chin point 224c of the mandible 224. The chin point 224c can be found by analyzed a border or a boundary of the mandible 224.

As shown in FIG. 1, FIG. 3 and FIG. 6C, operation S321 is performed by the processing unit 186 to read the scan record corresponding to this patient. The existed scan record may include the first coordinates of the first ROI(s) relative to the chin point 224c and the second coordinates of the second ROI(s) relative to the chin point 224c. The existed scan record may also record the historical logs about Bone Mass Content readings and Bone Mass Density readings of the all ROI(s) found in the body area 224a and the ramus area 224b.

As shown in FIG. 1, FIG. 3 and FIG. 6C, operation S322 is performed by the processing unit 186 to searching for the first ROI(s) in body area 224a and second ROI(s) in the ramus area 224b.

As shown in FIG. 1, FIG. 3 and FIG. 6C, operation S323 is performed by the processing unit 186 to calculate third coordinates of the first ROI(s) relative to the chin point 224c and fourth coordinates of the second ROI(s) relative to the chin point 224c.

As shown in FIG. 1, FIG. 3 and FIG. 6C, operation S324 is performed by the processing unit 186 to store the third coordinates into the scan record corresponding to the first ROI(s) and the fourth coordinates into the scan record corresponding to the second ROI(s). A difference between the first coordinates and the third coordinates in the scan record between two scans at different timings may indicate a displacement of the first ROI(s) over time. On the other hand, a difference between the second coordinates and the fourth coordinates in the scan record between two scans at different timings may indicates a displacement of the second ROI(s) over time.

As shown in FIG. 1, FIG. 3 and FIG. 6C, operation S325 is performed by the processing unit 186 to generate bone mineral analyzation data of first ROI(s) and bone mineral analyzation data of the second ROI(s) corresponding to the patient in this second scan. The bone mineral analyzation data may include numeric Bone Mass Content (BMC) of all ROIs and/or Bone Mass Density (BMD) of all ROIs. The bone mineral analyzation data obtained in the second scan can be different from the historical records in the first scan.

As shown in FIG. 1, FIG. 3 and FIG. 6C, operation S326 is performed by the processing unit 186 to compare bone mineral analyzation data to track bone mineral variation of first ROI(s) and second ROI(s). In an embodiment, the operation S326 is performed by the processing unit 186 to compare first bone mineral analyzation data of the first coordinates obtained in the first scan with third bone mineral analyzation data of the third coordinates obtained in the second scan, so as to track a first bone mineral variation of the first ROI(s) in the body area 224a. The operation S326 is performed by the processing unit 186 further to compare second bone mineral analyzation data of the second coordinates obtained in the first scan with fourth bone mineral analyzation data of the fourth coordinates obtained in the second scan, so as to track a second bone mineral variation of the second ROI(s) in the ramus area 224b.

Two areas of the mandible 224 are used by the application software for analysis. The body area 224a is a forward area of the mandible 224 located from the chin towards the submandibular fossa. The ramus area 224b is a rear area of the mandible 224. The ramus area 224b extends from the boundary of the body area 224a and the submandibular fossa to the condylar and coronoid processes.

On the initial study (e.g., the first scan) of a patient the system 100 and the method 300 will perform a search within the body area 224a of the mandible 224 to locate a specific area of lowest bone mass. The system 100 and the method 300 search for this area because conceptually this area will show the greatest percentage change in bone mineral content as the body area 224a performs the bone turnover process over time. At the same time, a similarly located ROI(s) in the ramus area 224b will be placed in the rear area of the bone. As programmed the location of these identified regions of interest (ROI) will remain constant in all mandible studies performed on a particular patient over time. Because the system 100 and the method 300 may search for the region of lowest bone mineral content and automatically place the two ROIs interest, and the two ROIs are suggested to be placed consistently between studies, the ROIs can be automatically selected by the system 100 and not adjustable or alterable by operators.

After a minimum of two mandible scans are performed on the same patient, the results of ROIs in the body area 224a and in the ramus area 224b can be compared between different scans. An outcome of the scan may further include a demonstration of the percentage change in bone mineral content (BMC) or bone mineral density (BMD) from one scan to the next scan. In addition, the outcome of the scan may further demonstrate if the mandible has gained or lost bone content. Additional studies over time will continue to provide more information for the patient about the rate of positive or negative change in the bone mineral content.

An embodiment of the disclosure offers the means to assess bone mineral content in located regions of the mandible with sufficient sensitivity to identify changes in bone mineral content in periods of months, so that response to disease or treatment can be swiftly identified. This capability comes about by means of the positioning system provided by the disclosure, by the use of pencil-beam geometry to assess comparable regions of the left and right mandible and by the use of search software that will identify the absolute target region in the body area and ramus area of the mandible.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A system for evaluating a patient, the system comprising:
a head supporting device, disposed on a first surface of an examination table for supporting the patient, the head supporting device comprising an adjustable headrest platform for supporting a head of the patient, the adjustable headrest platform is configured to be movable along a direction perpendicular to the first surface of the examination table;
an alignment checker, disposed on the examination table and located corresponding to the head of the patient, the alignment checker being configured to verify a location or an orientation of the head of the patient; and
a scanning device, configured for capturing a scan image corresponding to a mandible of the patient,
wherein the scanning device further comprises a processing unit, when a first scan is performed on the patient, the processing unit is configured to:
evaluate the scan image to locate a chin point of the mandible;
detect a body area and a ramus area of the mandible in the scan image;
search for a first region of interest in the body area and a second region of interest in the ramus area;
calculate first coordinates of the first region of interest relative to the chin point and second coordinates of the second region of interest relative to the chin point; and
store the first coordinates and the second coordinates in a scan record corresponding to the patient.

2. The system of claim 1, wherein the scanning device comprises:
a radiation emitting member configured for generating a scanning radiation in a route perpendicular to the first surface of the examination table, the route penetrates the mandible; and
a radiation detecting member configured for sensing the scanning radiation to generate the scan image, the radiation emitting member and the radiation detecting member are disposed on opposite sides relative to the examination table.

3. The system of claim 1, wherein when the patient is laid in a lateral recumbent position on the first surface, the adjustable headrest platform is configured to support at least a part of a temporal region or a parietal region of the head.

4. The system of claim 3, wherein when the adjustable headrest platform is moved along the direction perpendicular to the first surface, a height level of the adjustable headrest platform is adjusted, and the neck of the patient is flexible to rotate rightward or leftward according to the height level of the adjustable headrest platform.

5. The system of claim 1, wherein the alignment checker comprises a positioning grid, the positioning grid comprises:
a standing base; and
a transparent plate connected on the standing base, the transparent plate is located corresponding to a facial region of the patient, a plurality of marking grid lines are labeled on the transparent plate, wherein the location or the orientation of the head of the patient is verified by comparing facial features or facial contours to the marking grid lines.

6. The system of claim 5, wherein when the facial features or the facial contours are tilted by a tilt angle in reference to the marking grid lines, the adjustable headrest platform is moved from a first height level to a second height level according to the tilt angle, a difference between the first height level and the second height level is positively correlated to the tilt angle.

7. The system of claim 1, wherein when a second scan is performed on the patient after the first scan, the processing unit is adapted to:
locate the chin point of the mandible in the scan image;
read the scan record corresponding to the patient;
search for the first region of interest in the body area and the second region of interest in the ramus area;
calculate third coordinates of the first region of interest relative to the chin point and fourth coordinates of the second region of interest relative to the chin point; and
store the third coordinates into the scan record corresponding to the first region of interest and the fourth coordinates into the scan record corresponding to the second region of interest.

8. The system of claim 7, wherein the processing unit is configured to:
compare first bone mineral analyzation data of the first coordinates obtained in the first scan with third bone mineral analyzation data of the third coordinates obtained in the second scan to track a first bone mineral variation of the first region of interest in the body area; and
compare second bone mineral analyzation data of the second coordinates obtained in the first scan with fourth bone mineral analyzation data of the fourth coordinates obtained in the second scan to track a second bone mineral variation of the second region of interest in the ramus area.

9. A method for evaluating a patient, a head of the patient being supported by an adjustable headrest platform, the method comprising:
verifying a location or an orientation of the head of the patient;
adjusting a height level of the adjustable headrest platform according to a verifying result; and
capturing a scan image corresponding to a mandible of the patient,
wherein in operation of verifying the location or the orientation of the head of the patient, the method comprises:
comparing facial features or facial contours to marking grid lines labeled on a positioning grid; and
calculating a tilt angle of the facial features or the facial contours in reference to the marking grid lines.

10. The method of claim 9, wherein when the patient lay in a lateral recumbent position on the first surface, the adjustable headrest platform is configured to support at least a part of a temporal region or a parietal region of the head.

11. The method of claim 10, wherein when the adjustable headrest platform is moved along the direction perpendicular to the first surface, a height level of the adjustable headrest platform is adjusted, and the neck of the patient is flexible to rotate rightward or leftward according to the height level of the adjustable headrest platform.

12. The method of claim 9, wherein in operation of adjusting the height level of the adjustable headrest platform according to the verifying result, the method comprises:

moving the adjustable headrest platform from a first height level to a second height level according to the tilt angle, wherein a difference between the first height level and the second height level is positively correlated to the tilt angle.

13. The method of claim 9, wherein when a first scan is performed on the patient, the method further comprises:
    evaluating the scan image to locate a chin point of the mandible;
    detecting a body area and a ramus area of the mandible in the scan image;
    searching for a first region of interest in the body area and a second region of interest in the ramus area;
    calculating first coordinates of the first region of interest relative to the chin point and second coordinates of the second region of interest relative to the chin point; and
    storing the first coordinates and the second coordinates in a scan record corresponding to the patient.

14. The method of claim 13, wherein when a second scan is performed on the patient after the first scan, the method further comprises:
    locating the chin point of the mandible in the scan image;
    reading the scan record corresponding to the patient;
    searching for the first region of interest in the body area and the second region of interest in the ramus area;
    calculating third coordinates of the first region of interest relative to the chin point and fourth coordinates of the second region of interest relative to the chin point; and
    storing the third coordinates into the scan record corresponding to the first region of interest and the fourth coordinates into the scan record corresponding to the second region of interest.

15. The method of claim 14, wherein the method further comprises:
    comparing first bone mineral analyzation data of the first coordinates obtained in the first scan with third bone mineral analyzation data of the third coordinates obtained in the second scan to track a first bone mineral variation of the first region of interest in the body area; and
    comparing second bone mineral analyzation data of the second coordinates obtained in the first scan with fourth bone mineral analyzation data of the fourth coordinates obtained in the second scan to track a second bone mineral variation of the second region of interest in the ramus area.

16. A system for positioning the head of a patient for radiation imaging, comprising:
    adjustable head supporting means for providing an adjustable headrest platform movable along a direction;
    aligning means for verifying a location and an orientation of the head of the patient; and
    adjusting means for moving the adjustable headrest platform along the direction according to a result generated by the aligning means,
    wherein the adjustable head supporting means comprises a head supporting device, the head supporting device comprises:
    a base member fixed on an examination table;
    an adjustable headrest platform configured for supporting a head of the patient; and
    a lifting member, connected between the base member and the adjustable headrest platform, the lifting member being configured for carrying the adjustable headrest platform to move from a first height level to a second height level relative to the base member.

17. The system in claim 16, wherein the aligning means comprises a positioning grid, the positioning grid comprises:
    a standing base; and
    a transparent plate connected on the standing base, the transparent plate is located corresponding to a facial region of the patient, and a plurality of marking grid lines are labeled on the transparent plate.

* * * * *